United States Patent
Richter

Patent Number: 6,149,395
Date of Patent: Nov. 21, 2000

[54] SUCTION PULSATOR

[76] Inventor: Siegfried Richter, Himmelreich 9, D-88605 Sauldorf-Rast, Germany

[21] Appl. No.: 09/197,204

[22] Filed: Nov. 20, 1998

[30] Foreign Application Priority Data

Dec. 11, 1997 [DE] Germany .......................... 297 21 567

[51] Int. Cl.[7] .................. F04F 5/48; A61M 1/06
[52] U.S. Cl. .................. 417/182; 417/198; 137/624.14; 604/74
[58] Field of Search .................. 417/151, 182, 417/183, 184, 185, 198; 137/624.14, 903, 875; 604/74

[56] References Cited

U.S. PATENT DOCUMENTS

| | | | |
|---|---|---|---|
| 334,852 | 1/1886 | Eberman | 417/184 |
| 2,908,227 | 10/1959 | McDougall | 417/182 |
| 3,146,726 | 9/1964 | Sidebottom | 417/198 |
| 4,961,726 | 10/1990 | Richter | 604/74 |

FOREIGN PATENT DOCUMENTS

| | | |
|---|---|---|
| 0 123 269 A2 | 10/1984 | European Pat. Off. . |
| 553664 | 5/1923 | France .................. 417/185 |
| 22 41 233 B2 | 9/1980 | Germany . |
| 32 19 628 A1 | 12/1983 | Germany . |
| 28 12 830 C2 | 8/1987 | Germany . |
| 3 378 282 C2 | 5/1991 | Germany . |

*Primary Examiner*—Charles G. Freay
*Attorney, Agent, or Firm*—McGlew and Tuttle, P.C.

[57] ABSTRACT

A suction pulsator (1) used to periodically generate a vacuum in a container connected to it, especially in a collection container for mother's milk, which is provided with a suction funnel. A central nozzle hole (25) of a nozzle body (20) is provided, wherein a compressed air flow flows through the nozzle hole (25) and the nozzle body (20) is concentrically surrounded by a ring-shaped suction gap (35), wherein the nozzle (25) opens into a narrow, radial outlet gap (36), which is formed between a radial deflecting surface (40), which guides the compressed air flow over the suction gap (35), and annular surfaces (29, 30) of the nozzle body (20) and of a nozzle jacket (13), which concentrically surround the nozzle hole (25) and the suction gap (35). The suction gap (35) opening openly into the outlet gap (36) is in connection with a suction line (39), which can be connected to the collection container through a connection opening (38), which is arranged away from the outlet gap (36).

23 Claims, 6 Drawing Sheets

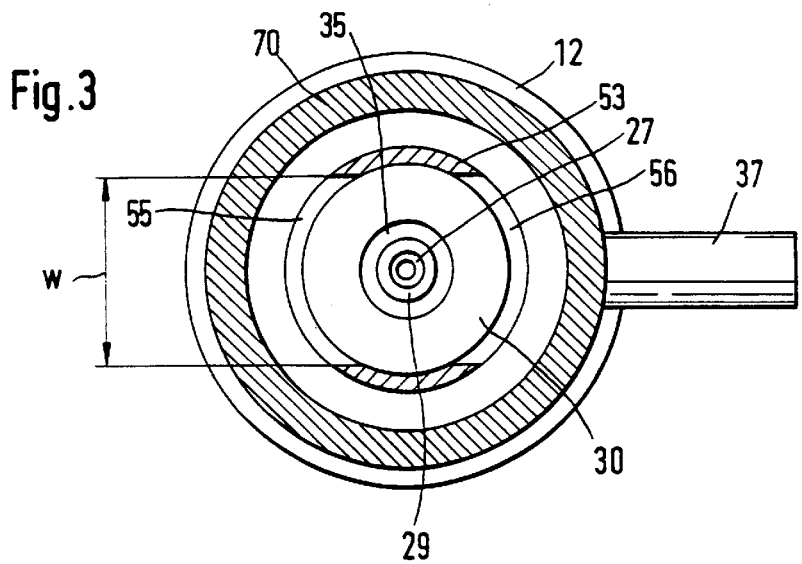
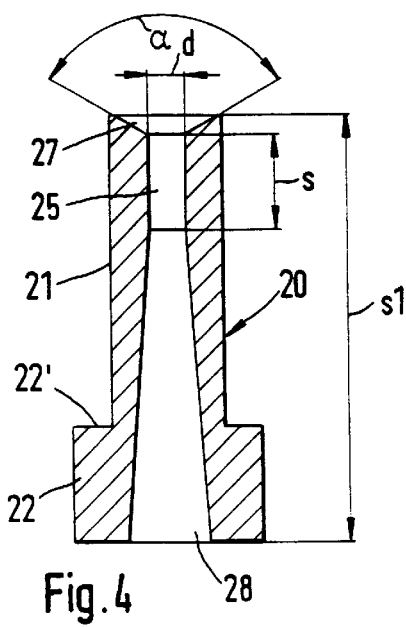
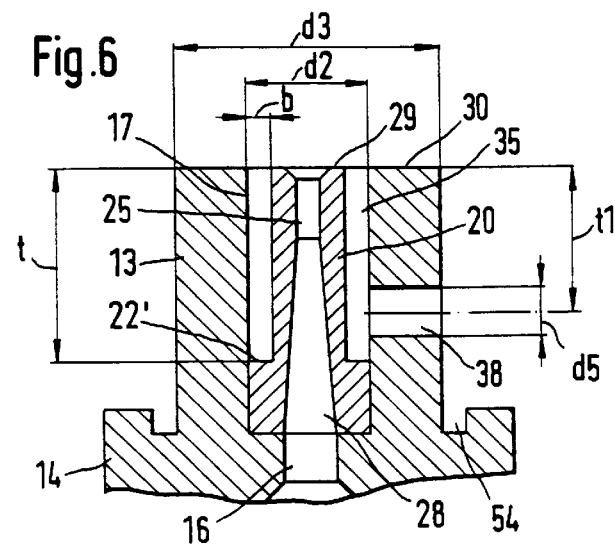
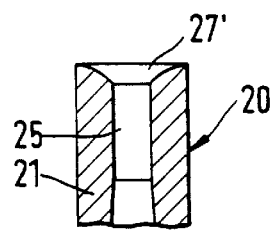
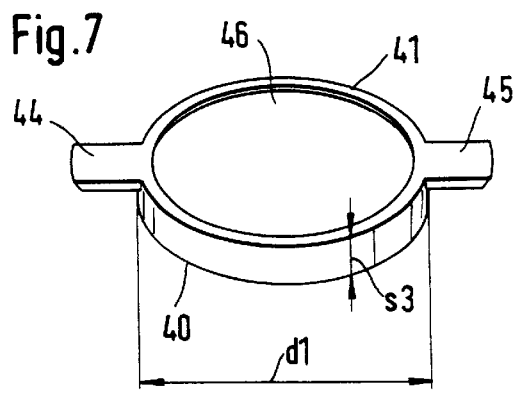

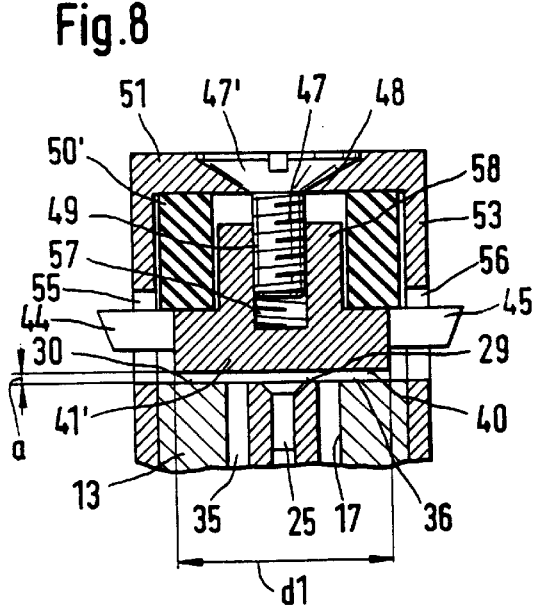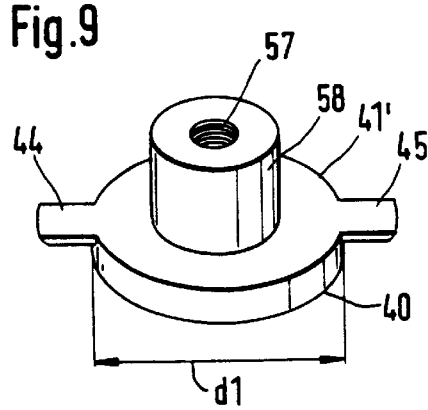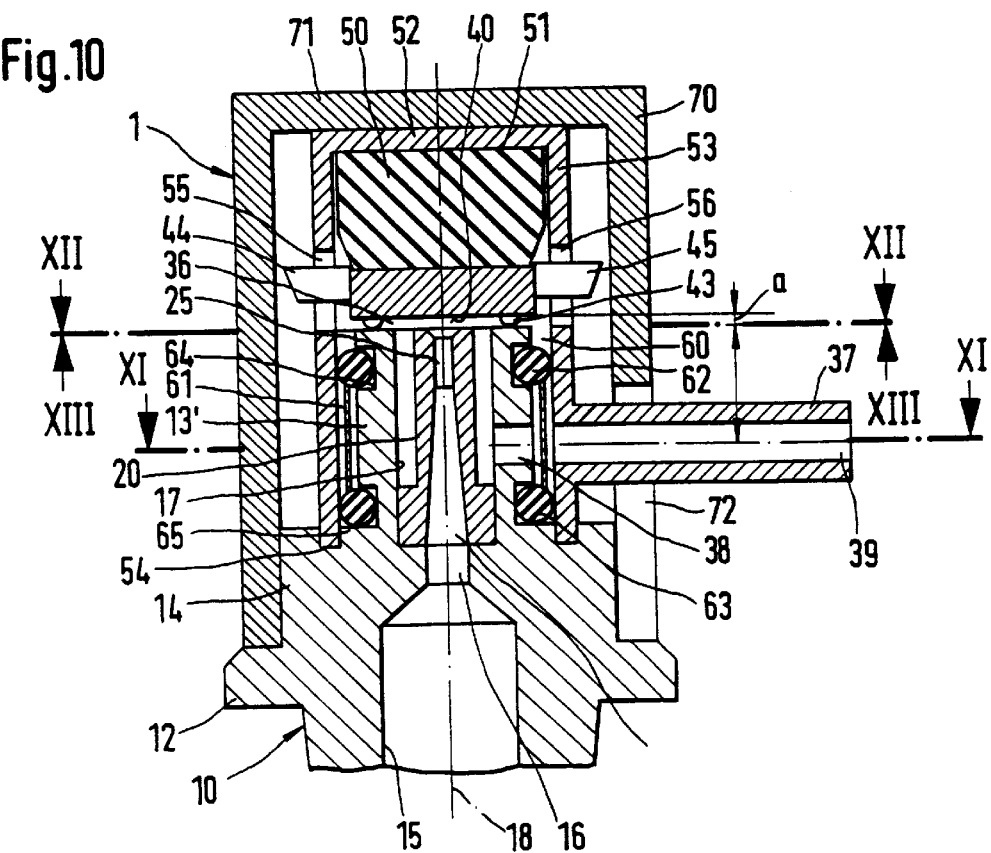

SUCTION PULSATOR

FIELD OF THE INVENTION

The present invention pertains to a suction pulsator for periodically generating a vacuum in a connected container, especially in a collection container for mother's milk, which is provided with a suction funnel.

BACKGROUND OF THE INVENTION

A mother's milk pump has already been known (DE 37 38 282 C2), which is connected to a collection vessel provided with a suction funnel via a pulsator by means of a suction line. In a two-chamber housing, the pulsator has an air chamber, to which atmospheric pressure is admitted, and a vacuum chamber, which is located between the suction pump and the collection vessel due to two connections. In addition, a closing member is provided, which is actuated by a control member arranged movably to and fro between the vacuum chamber and the air chamber.

While this prior-art pulsator, which is needed to operate a mother's milk pump, has only one valve, other mother's milk pumps or milk pumps have been known (SU-4-6 52588), in which the periodical opening and closing of a valve interrupting the suction flow is controlled by an electronically operating pulse generator.

In other prior-art milk pumps (EP-01 23 269 A2, DE-32 19 628 A1, DE-22 41 233 B2, DE 28 12 830 C2), the means corresponding to a pulsator have a substantially more complicated design, because a plurality of valves are provided there, whose actuation requires special auxiliary means, which are designed as pistons and diaphragms.

The prior-art milk pumps can consequently be operated only with a means operating as a pulsator, which is used in a suction air flow, which is usually generated by a vacuum pump.

SUMMARY AND OBJECTS OF THE INVENTION

The basic object of the present invention is to provide a suction pulsator of the type described in the introduction, which has a simpler design, can be manufactured less expensively, can be operated more simply, and can be used universally without an additional suction pump, and which generates the suction flow itself.

This object is accomplished according to the present invention in that a central nozzle hole of a nozzle body, wherein a comp ressed air flow flows through the nozzle hole and wherein the nozzle body is concentrically surrounded by a ring-shaped nozzle gap, opens into a narrow, radial outlet gap, which is formed between a radial deflecting surface, which guides the compressed air flow over the suction gap, and annular surfaces of the nozzle body and of a nozzle jacket, which concentrically surround the nozzle hole and the suction gap, and in that the suction gap opening openly into the outlet gap is in connection with a suction line, which can be connected to the collection container, through a connection opening arranged away from the outlet gap.

It is possible due to the solution according to the present invention to use a compressed air-operated suction nozzle such that by means of a preferably continuous or approximately constant compressed air flow, it builds up a vacuum with an approximately constant (negative) maximum in a pulse-like manner in periods following each other uninterruptedly, which vacuum collapses in the rhythm of the period after the respective maximum has been reached and is built up again, in a closed system that contains a suction line, a collection container and a suction funnel, which is connected to the collection container and is tightly attached to the breast of a breastfeeding mother. It is not absolutely necessary for the compressed air flow to be uniformly constant. For instance, a compressed air flow pulsating according to a sine curve, which does not drop below the positive value of the desired vacuum, may be sufficient as well.

Another important advantage of the device according to the present invention is that it contains no moving parts, which would be subject to wear, and that it can be assembled, on the whole, from very few individual parts, from only three individual parts in the most favorable case, wherein another advantage lies in the fact that these individual parts may consist of a plastic or metal and the plastic parts can be manufactured at a very low cost in large lots.

To optimize the actual operation of the pulsator a radial width of the suction gap is less than a diameter of the central nozzle hole, and is preferably one third of a diameter of the central nozzle hole. An axial length of the suction gap is greater than or equal to an external diameter of the suction gap. The suction connection opening is a radial hole with a diameter greater than or equal to one and a half times a diameter of the central nozzle hole, and the suction connection opening is spaced an axial distance from the radial outlet gap by an amount that is greater than or equal to an external diameter of the suction gap. The end of the nozzle body and the nozzle jacket each include an annular surface. The annular surface of the nozzle body and the nozzle jacket are substantially parallel to the radial deflecting surface. The radial deflecting surface and the annular surface of the nozzle body and the nozzle jacket are substantially perpendicular to an axis of the central nozzle hole and are smoothly polished. An axial width of the radial outlet gap corresponds to less than or equal to one third a diameter of the central nozzle hole. The radial deflecting surface has a diameter greater than an external diameter of the suction gap, by at least a width of the suction gap. An external diameter of the annular surface is greater than or equal to a diameter of the radial deflecting surface. The central nozzle hole has a discharge end adjacent the radial deflecting surface, the discharge end having one of a conical and a trumpet shaped expansion. The conical shaped expansion has a cone angle greater than or equal to 90°, and preferably 120 degrees. The trumpet shaped expansion continuously leads over into the annular surface of the nozzle body without formation of an annular edge.

The following features of the present invention offer special advantages in terms of the manufacturing technology. The radial deflecting surface is formed by a flat front surface of a movably mounted deflecting plate which is held under an axial spring pressure with an axial spacer at a spaced location from the annular surfaces. The axial spacer includes cam-like projections in the radial deflecting surface and the cam-like projections are in contact with one of the annular surfaces. A sleeve body is substantially concentric with the suction gap and includes an end wall. An axial adjusting screw is in connection with the deflecting plate by a threaded engagement, and the adjusting screw includes a screw head supported at the front wall of the sleeve body. The adjusting screw forms the spacer. The sleeve body includes a connecting branch adjacent the suction connection opening. A spring element is supported by the end wall and biases the deflecting plate with the spacer against the annular surfaces.

Hygienic requirements are met by the arrangement of a filter arranged between the suction connection opening and the suction line. The interior of the sleeve body and an exterior of the nozzle jacket define an annular filter gap. The filter is tubular and is arranged in the filter gap between the suction connection opening and the suction line.

A simple possibility of easy cleaning of the inherently very narrow outlet gap is provided by a wall perforation defined by said sleeve body and corresponding to a thickness and a diameter of the deflecting plate. The wall perforation passes compressed air and the deflecting plate to an outside environment.

A protective housing surrounds the sleeve body and is detachably fastened to a nozzle connection to additionally protect the suction pulsator from harmful external effects.

The nozzle body, the nozzle jacket, the radial deflecting surface, and the suction line are arranged on a cover of the container, and a nozzle connection is attached to the nozzle jacket and connectable to a pressure line to keep particles of the mother's milk from being drawn in and deposited in a suction line between the suction pulsator and the collection container.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is a section III—III from FIG. 1;

FIG. 4 is an enlarged representation of a sectional view of the nozzle body;

FIG. 5 is a sectional view of the upper end section of the nozzle body according to FIG. 4, but with another shape of the nozzle end;

FIG. 6 is an enlarged representation of a sectional view of part of the nozzle connection with the nozzle body inserted;

FIG. 7 is an enlarged representation of an individual part from FIG. 1;

FIG. 8 is a detail from FIG. 1 in a modified embodiment;

FIG. 9 is a perspective view of an individual part from FIG. 8;

FIG. 10 is a sectional view of an embodiment of the suction pulsator that was modified compared with the embodiment according to FIG. 1;

DESCRIPTION OF THE PREFERRED EMBODIMENT

Figure 14:
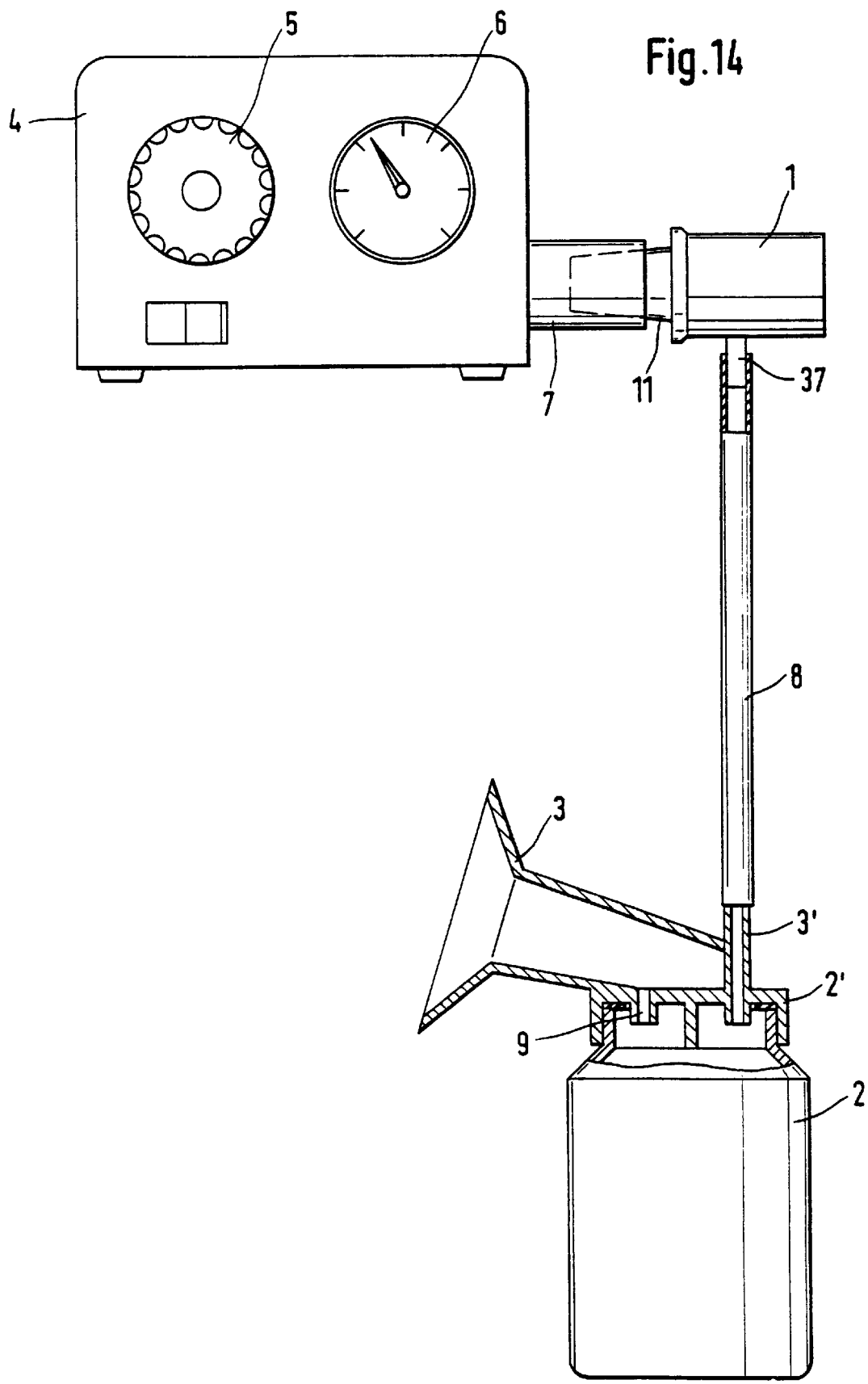
FIG. 14 is a view of a mother's milk pump, comprising a compressed air generator, the suction pulsator according to the present invention and a collection container with suction funnel.
Figure 15:
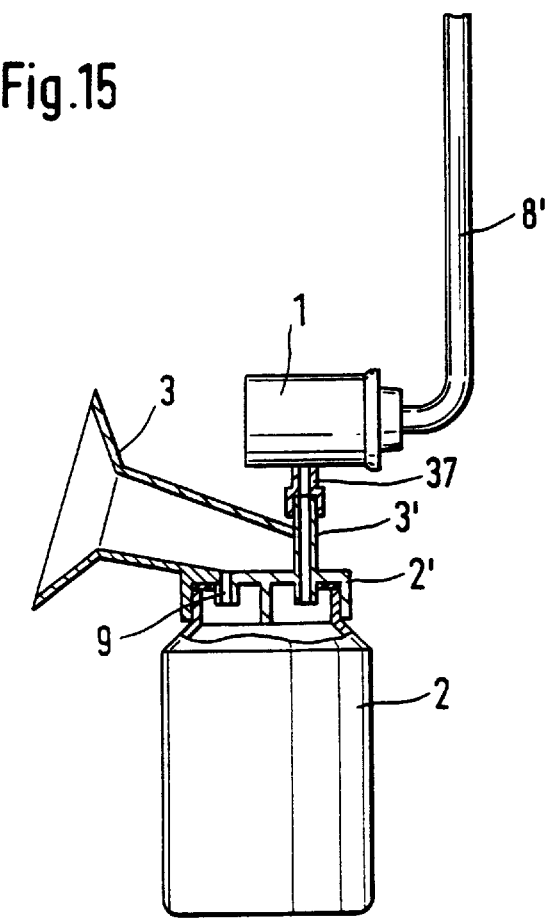
FIG. 15 is a view of a collection container with the suction pulsator attached on a smaller scale.

As can be recognized from FIGS. 14 and 15, the suction pulsator 1 according to the present invention is part of a mother's milk pump, which has a collection container 2 for the mother's milk with a suction funnel 3, which can be attached to the breast of a breastfeeding mother, and a compressed air generator 4 (compressor).

The compressed air generator 4 generates a preferably constant compressed air flow, whose intensity can be regulated within certain limits by means of a setting button 5 and is indicated by means of a pressure gage 6. In the arrangement according to FIG. 14, the suction pulsator 1 is connected to the compressed air generator 4 via a connecting branch 7. Via a suction line 8, the suction pulsator 1 is connected on the suction side to a connecting branch 3' of a removable cover 2' of the collection container 2. The collection container 2 is in turn in connection with the hollow space of the suction funnel 3 via a hole 9. The suction funnel 3 and the connecting branch 3' are one-piece components of the cover 2'.

In the arrangement according to FIG. 15, the suction pulsator 1 is arranged directly on the connecting branch 3' of the cover 2' and is connected to same on the suction side through a connecting branch 37. This arrangement is possible without problems because of the small size of the suction pulsator 1 and its low weight and it is also advantageous, because the long suction line 8 is eliminated and a pressure line 8', in which no particles of the mother's milk drawn in can settle, may be used, instead, for the connection to the compressed air generator 4.

The suction pulsator 1 is used to periodically generate a vacuum in the collection container 2 and in the suction funnel 3 when the latter is attached to the breast of a breastfeeding mother. If no ambient air can enter the collection container 2, while air is being drawn in by the suction pulsator via the suction line 8, vacuum is generated in the collection container 2 and in the hollow space of the suction funnel 3.

The suction pulsator comprises a nozzle connection 10, whose basic shape is round and has mostly cylindrical parts, which are arranged coaxially to a central axis 18. The nozzle connection comprises a connection cone 11, a ring flange 12 as well as a cylindrical nozzle jacket 13, which forms the axial, radially offset continuation of a cylindrical attachment 14, which is arranged on the side of the ring flange 12 located opposite the cone 11.

A central axial hole 15, which opens via a connection hole 16 of a smaller diameter into a cylindrical hole 17, which is coaxial thereto and is located in the nozzle jacket 13, is located in the nozzle connection 10. A cylindrical sleeve body 20 is inserted into the hole 17, and the sleeve body 20 has a nozzle neck 21 of reduced diameter and a base part 22, whose diameter is adapted to the internal diameter of the hole 17.

Figure 1:
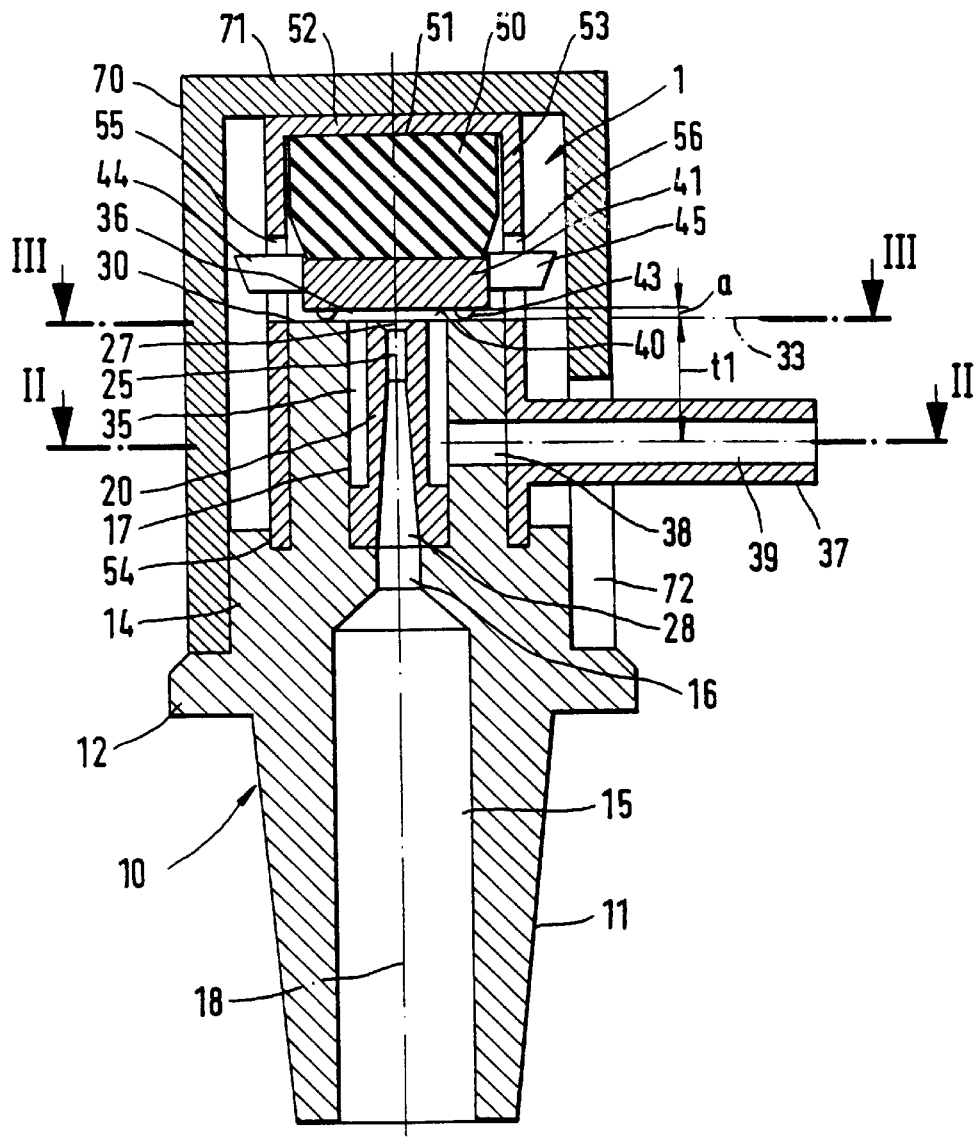
FIG. 1 is a sectional view of a suction pulsator.
Figure 2:
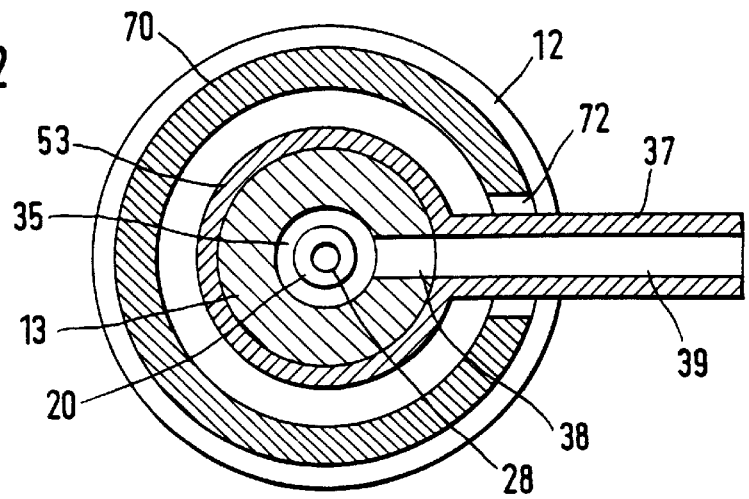
FIG. 2 is a section II—II from FIG. 1.
Figure 11:
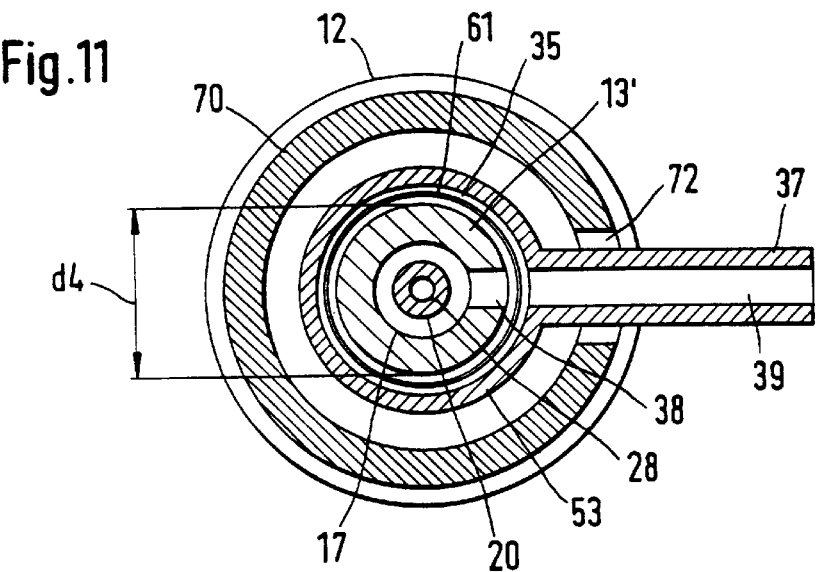
FIG. 11 is a section XI—XI from FIG. 10.

The nozzle body 20, represented as an individual part in FIG. 4, is provided at its discharge-side end section with a cylindrical nozzle hole 25, which has an expansion 27 (FIG. 4) or 27' (FIG. 5) on the discharge side, and the expansion may be conical or trumpet4ike. In the case of the conical design of this expansion 27 according to FIG. 4, the cone angle a should be at least 90°, but preferably 120°. If the expansion 27' has a trumpet-like design according to FIG. 5, i.e., if it has a convexly arched annular surface, an edgeless transition to the annular surface 29, which may be functionally advantageous, can be established more easily. On the side of the incoming flow, a conical hole 28, whose incoming flow-side end diameter approximately corresponds to the diameter of the connection hole 16 in the nozzle connection 10, joins the nozzle hole 25, so that, as is shown in FIG. 1 and FIG. 2, a stepless transition is present between the connection hole 16 and the conical hole 28 of the nozzle body 20.

The axial length s of the nozzle hole 25 is somewhat more than double its diameter d in the exemplary embodiment. However, it is sufficient for a good mode of operation and function for the length s of the nozzle hole 25 to be at least equal to the diameter d.

The overall length s1 of the nozzle body 20 exactly corresponds to the axial depth of the hole 17 in the nozzle jacket 13, so that the flat residual annular surface 29 of the nozzle body 20 is located at the same radial level 33 (FIG. 1) as the likewise flat front-side annular surface 30 of the nozzle jacket 13.

The nozzle body 20 with its nozzle hole 25 and with its conical hole 28 is a compressed air nozzle, through which a constant compressed air flow flows under a flow pressure of, e.g., 0.8 bar during the operation. This compressed air nozzle is surrounded by a ring-shaped, concentric suction gap 35, which is limited by the cylindrical wall of the nozzle neck 21, on the one hand, and by the inner surface of the hole 17 as well by a radial shoulder 22' of the base part 22, on the other hand.

The nozzle hole 25 with its expansion 27 or 27' opens in a narrow radial outlet gap 36. This outlet gap 36 is formed between a radial deflecting surface 40, which guides the compressed air flow over the suction gap 35, and the annular surfaces 29 and 30 of the nozzle body 20 and of the nozzle jacket 13, respectively, which concentrically surround the nozzle hole 25 and the suction gap 35.

The width b (FIG. 6) of the suction gap 35 is smaller than the diameter d of the nozzle hole 25. The width b of the suction gap approximately corresponds to about one third of the diameter d of the nozzle hole 25.

The depth t of the suction gap 35 approximately corresponds to about three times its external diameter d2 in the exemplary embodiment, and this external diameter d2 corresponds to at least two and a half times the diameter d of the nozzle hole 25. However, it is also sufficient for the depth t to be at least equal to the external diameter d2.

The suction gap 35 opening openly into the outlet gap 36 is connected by a suction connection opening 38 located away from the outlet gap 36 to the hole 39 of a connecting branch 37. The suction connection opening 38 comprises a radial hole in the nozzle jacket 13, whose diameter d5 may be approximately equal to the diameter d of the nozzle hole 25, but which is preferably about 1.5 times larger than the diameter d.

As can be best recognized from FIGS. 1 and 6, the connection opening 38 has an axial distance t1 from the outlet gap 36 or from the annular surfaces 29 and 30, which distance corresponds to at least 2.5 to 3 times the external diameter d2 of the suction gap 35.

The circumferential surfaces 40 limiting the outlet gap 36, on the one hand, and the annular surfaces 29 and 30 of the nozzle body 20 and of the nozzle jacket 13, which are located in parallel opposite them, on the other hand, are flat and smooth. An improvement in the suction effect can be achieved by polishing the deflecting surface 40.

The axial width a of the outlet gap 36, which should correspond at most to one third the diameter d of the nozzle hole, is also of great significance for the function. In the case of a diameter d of, e.g., 0.9 mm, the axial width a of the outlet gap 36 may be 0.1 mm to 0.3 mm, depending on the intensity of the compressed air flow. To ensure satisfactory operation, the deflecting surface 40 must completely cover the suction gap 35. The diameter d1 of the deflecting surface should therefore be greater by at least the width b than the external diameter d2 of the suction gap 35 (FIG. 6).

The external diameter d3 of the annular surface 39 surrounding the suction gap 35 may now be equal to the diameter d1 of the deflecting surface 40.

The deflecting surface 40 is formed by a flat front surface of a deflecting plate 41, which is mounted immovably per se and is held under an axial spring pressure with at least one axial spacer at a distance a from the annular surfaces 29 and 30. The spacers may consist of cam-like projections 43, which are arranged in the deflecting surface 40 and lie, e.g., on the annular surface 39 of the nozzle jacket 13.

This embodiment is shown in FIGS. 1 through 7, 9 and 13, wherein the deflecting plate 41 is represented as an individual part in FIG. 7. The deflecting plate 41 is provided with two diametrically opposed fingers 44 and 45 and with a circular depression 46 on the top side. Into this depression 46 extends the lower, conical end section of a rubber-elastic pressure body 50, which generates the above-mentioned spring force, has an essentially cylindrical shape and is in supporting contact by a flat front surface 51 with the inside of a front or end wall 52 of a cylindrical sleeve body 53.

With its lower end, the sleeve body 53 is firmly seated in an annular groove 54 of the nozzle connection 10. The radially outwardly projecting connection branch 37, to which the suction line 8 is connected, is made in one piece with the sleeve body 53, which surrounds the nozzle jacket 13 without a clearance in the embodiment according to FIGS. 1 through 3 (FIG. 14).

In the area of the deflecting plate 41 and of the outlet gap 36, the cylindrical wall of the nozzle body 53 is provided with two diametrically opposed, segment-like perforations 55 and 56, through which the compressed air flowing out in the radial direction through the outlet gap 36 can escape to the outside.

Since the pressure body 50 consists of a spring-elastic material, it is possible to lift off the deflecting plate 41 from the annular surfaces 29, 30 against the spring force of the pressure body 50 in order to, e.g., clean the outlet gap 36. The fingers 44, 45 may be used for this purpose.

Figure 12:
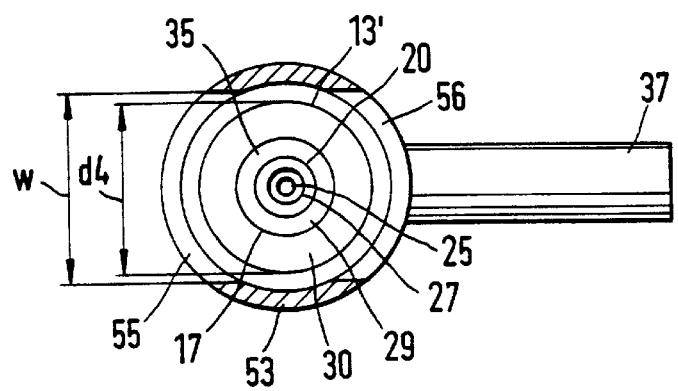
FIG. 12 is a section XII—XII from FIG. 10.
Figure 13:
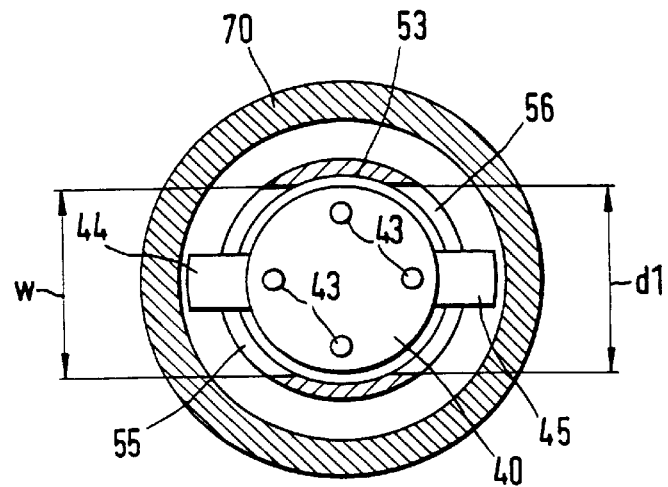
FIG. 13 is a section XIII—XIII from FIG. 10.

To make it possible to remove the plate 41 from the sleeve body 53 for cleaning or replacement, the two perforations have a width w (FIGS. 12 and 13) that corresponds to the diameter d1 of the plate 41, and their axial extension is somewhat greater than the thickness s3 of the plate 41 (FIG. 7).

In the embodiment shown in FIGS. 8 and 9, a plate 41' is provided, which is arranged in the same manner as the plate 41, but is held by means of a spacer, which comprises an adjusting screw 47, whose screw head 47' is mounted in a recessed hole 48 of the front wall 51 of the sleeve body 53, and which screw is connected to the plate 41' by a threaded engagement 49. The adjusting screw 47 is screwed into a threaded hole 57 of a cylindrical attachment 58 arranged on the top side. This threaded hole 57 is surrounded by a ring-shaped spring- or rubber-elastic pressure body 50', which maintains the plate 41' in its axial position under a certain pretension. This axial position of the plate 41' may be adjusted by means of the adjusting screw 47, which is screwed into the threaded hole 57 to varying degrees. The adjusting screw 47 is thus used as an adjustable spacer for the plate 41 with its flat, smooth, preferably polished deflecting surface 40 located opposite the nozzle hole 25. The plate 41' is also provided with the radially projecting fingers 44 and 45, whose purpose is the same as in the case of the plate 41.

In the embodiment of the suction pulsator 1 shown in FIGS. 10 through 13, the nozzle connection 10 is provided with a nozzle jacket 13', whose external diameter d4 (FIG. 11) is smaller than the internal diameter of the sleeve body 53 surrounding this nozzle jacket 13'. As a result, there is an annular gap 60 between the nozzle jacket 13' and the sleeve body 53 as well. A tubularly designed filter 61, which is arranged between two sealing rings 62 and 63 and thus also between the connection opening 38 and the hole 39 of the connecting branch 37, is located in the annular gap 60.

This tubular filter 61 serves the purpose of trapping contaminants of the air drawn in and of preventing them from entering the outlet gap 36 or into the atmosphere through the suction gap 35.

The two sealing rings 62, 63 are positioned in recessed annular grooves 64 and 65 of the nozzle jacket 13' axially above and below the connection opening 38 and have the task of sealing the section of the annular gap 60, in which the filter 61 is accommodated, as well as the two ends of the filter 61 from the outside. The design and the mode of operation of this suction pulsator 1 equipped with the filter 61 is otherwise the same as that of the other embodiments.

Due to the presence of the annular gap 60, it is not necessary to arrange the connecting branch 37 coaxially to the connection opening 38 designed as a radial hole. The connecting branch 37 may be arranged, instead, in any desired position in the circumferential direction, the only important thing being that its hole 39 be in connection with the section of the annular gap 60 located between the two sealing rings 62 and 63.

For protection against external effects, the sleeve body 53 is provided with a cylindrical protective housing, which completely surrounds it, has a closed upper front wall 71 and is fastened to the cylindrical attachment 14 of the nozzle connection 10 in a firmly seated but removable manner. To accommodate the radially outwardly projecting connecting branch 37, a slot-like opening 72 is provided in the wall of the protective housing 70.

The mode of operation of the above-described suction pulsator 1 is based on the fact that the (preferably continuous) compressed air flow flowing through the nozzle hole 25 and deflected by the deflecting surface 40 in the radial direction via the suction gap 35 generates a vacuum due to its suction effect in the suction gap 35 and in the collection container 2, which is in connection with it via the connection opening 38, the connecting branch 37 and the suction line 8, as well as in the suction funnel 3 of the latter when the suction funnel 3 is closed, corresponding to its purpose, i.e., e.g., when it is attached to the breast of a breastfeeding mother. As soon as the vacuum has reached a certain maximum, which is, with a negative sign, about two thirds to three fourths the flow pressure of the compressed air flow and an equilibrium has been reached within the system, the suction effect is briefly interrupted. The vacuum is again filled up, at least for the most part, after which the suction effect can begin again in order to build up a vacuum again.

Figure 16:
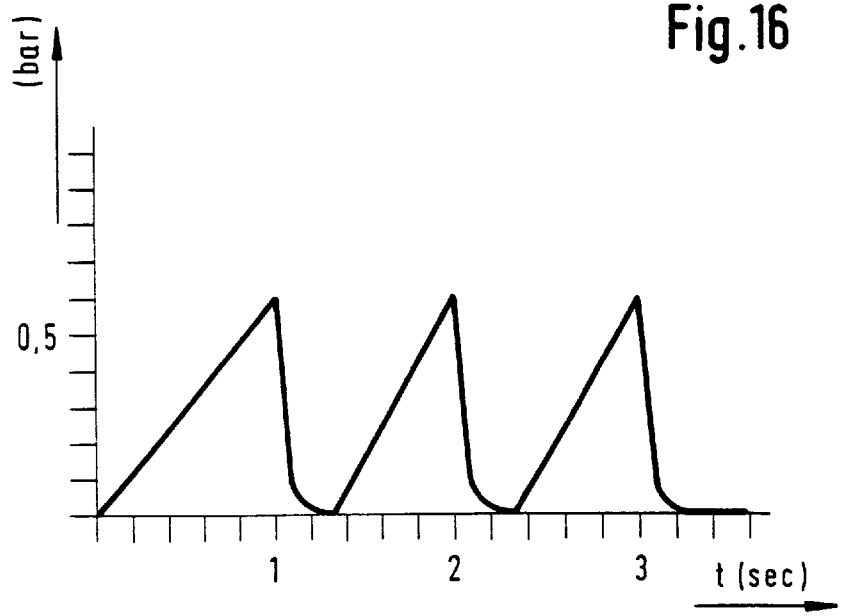
FIG. 16 is a function diagram.

This happens in a periodic sequence, which is schematically shown in the diagram in FIG. 16. The sawtooth-like curve represents the periodic buildup of the vacuum, the duration of the period being about 1 sec.

The duration of this period may be influenced by changing the compressed air flow and/or by changing the outlet gap 36. Another possibility of influencing the duration of the period is to change the intensity of the suction by throttling the outgoing air flow to varying degrees. The duration of the period also depends on the overall air volume of the system.

While specific embodiments of the invention have been shown and described in detail to illustrate the application of the principles of the invention, it will be understood that the invention may be embodied otherwise without departing from such principles.

What is claimed is:

1. A suction pulsator for periodically generating a vacuum in a container, the pulsator comprising:

a nozzle body defining a central nozzle hole connectable to a compressed air source;

a nozzle jacket surrounding said nozzle body, an inside of said nozzle jacket and an outside of nozzle body define a suction gap substantially concentric with said central nozzle hole;

a radial deflecting surface spaced from an end of said nozzle body and said nozzle jacket to define a radial outlet gap, said radial outlet gap being in communication with said central nozzle hole and said suction gap, said radial deflecting surface guiding air from said central nozzle hole over said suction gap;

a suction connection opening in communication with said suction gap and spaced from said radial outlet gap;

a suction line in communication with said suction connection opening.

2. A pulsator in accordance with claim 1, wherein:

a radial width of said suction gap is less than a diameter of said central nozzle hole.

3. A pulsator in accordance with claim 1, wherein:

a radial width of said suction gap is approximately one third of a diameter of said central nozzle hole.

4. A pulsator in accordance with claim 1, wherein:

an axial length of said suction gap is greater than or equal to an external diameter of said suction gap.

5. A pulsator in accordance with claim 1, wherein:

said suction connection opening is a radial hole with a diameter greater than or equal to one and a half times a diameter of said central nozzle hole, said suction connection opening being spaced an axial distance from said radial outlet gap by an amount that is greater than or equal to an external diameter of said suction gap.

6. A pulsator in accordance with claim 1, wherein:

said end of said nozzle body and said nozzle jacket each include an annular surface, said annular surface of said nozzle body and said nozzle jacket are substantially flat and substantially parallel to said radial deflecting surface, said radial deflecting surface and said annular surface of said nozzle body and said nozzle jacket are substantially perpendicular to an axis of said central nozzle hole.

7. A pulsator in accordance with claim 6, wherein:

said radial deflecting surface is polished.

8. A pulsator in accordance with claim 1, wherein:

an axial width of said radial outlet gap corresponds to less than or equal to one third a diameter of said central nozzle hole.

9. A pulsator in accordance with claim 1, wherein:

said radial deflecting surface has a diameter greater than an external diameter of said suction gap, by at least a width of said suction gap.

10. A pulsator in accordance with claim 9, wherein:

said end of said nozzle jacket includes an annular surface surrounding said suction gap, an external diameter of said annular surface is greater than or equal to a diameter of said radial deflecting surface.

11. A pulsator in accordance with claim 1, wherein:

said end of said nozzle body and said nozzle jacket each include an annular surface;

said radial deflecting surface is formed by a flat front surface of a movably mounted deflecting plate which is held under an axial spring pressure with an axial spacer at a spaced location from said annular surfaces.

12. A pulsator in accordance with claim 11, wherein:

said axial spacer includes cam-like projections in said radial deflecting surface and said cam-like projections are in contact with one of said annular surfaces.

13. A pulsator in accordance with claim 11, further comprising:

a sleeve body substantially concentric with said suction gap and including an end wall;

an axial adjusting screw in connection with said deflecting plate by a threaded engagement, said adjusting screw including a screw head supported at said front wall of said sleeve body, said adjusting screw formiing said spacer.

14. A pulsator in accordance with claim 13, wherein:

said sleeve body includes a connecting branch adjacent said suction connection opening.

15. A pulsator in accordance with claim 13, wherein:

a spring element is supported by said end wall and biases said deflecting plate with said spacer against said annular surfaces.

16. A pulsator in accordance with claim 1, wherein:

said central nozzle hole has a discharge end adjacent said radial deflecting surface, said discharge end having one of a conical and a trumpet shaped expansion.

17. A pulsator in accordance with claim 1, wherein:

said central nozzle hole has a discharge end adjacent said radial deflecting surface, said discharge end having a conical shaped expansion with a cone angle greater than or equal to 90°.

18. A pulsator in accordance with claim 1, wherein:

said end of said nozzle body includes an annular surface;

said central nozzle hole has a discharge end adjacent said radial deflecting surface, said discharge end has a trumpet shaped expansion continuously leading over into said annular surface of said nozzle body without formation of an annular edge.

19. A pulsator in accordance with claim 1, wherein:

a filter is arranged between said suction connection opening and said suction line.

20. A pulsator in accordance with claim 1, wherein:

a sleeve body is substantially concentric with said suction gap and includes a connecting branch adjacent said suction connection opening, an interior of said sleeve body and an exterior of said nozzle jacket defining an annular filter gap;

a tubular filter is arranged in said filter gap between said suction connection opening and said suction line.

21. A pulsator in accordance with claim 1, wherein:

said radial deflecting surface is formed by a flat front surface of a movably mounted deflecting plate;

a sleeve body is substantially concentric with said suction gap and defines a wall perforation corresponding to a thickness and a diameter of said deflecting plate, said wall perforation passing compressed air and said deflecting plate to an outside environment.

22. A pulsator in accordance with claim 13, wherein:

a protective housing surrounds said sleeve body and is detachably fastened to a nozzle connection.

23. A pulsator in accordance with claim 1, wherein:

said nozzle body, said nozzle jacket, said radial deflecting surface, and said suction line are arranged on a cover of the container;

a nozzle connection is attached to said nozzle jacket and connectable to a pressure line.

\* \* \* \* \*